United States Patent
Hess et al.

(10) Patent No.: US 10,478,183 B2
(45) Date of Patent: Nov. 19, 2019

(54) ADJUNCT RELEASE FOR SURGICAL STAPLERS

(71) Applicant: Ethicon LLC, Guaynabo, PR (US)

(72) Inventors: Christopher J. Hess, Blue Ash, OH (US); Frederick E. Shelton, IV, Hillsboro, OH (US); Jason L. Harris, Lebanon, OH (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 247 days.

(21) Appl. No.: 15/436,070

(22) Filed: Feb. 17, 2017

(65) Prior Publication Data
US 2018/0235614 A1    Aug. 23, 2018

(51) Int. Cl.
*A61B 17/072* (2006.01)

(52) U.S. Cl.
CPC .. *A61B 17/072* (2013.01); *A61B 2017/07257* (2013.01); *A61B 2017/07271* (2013.01)

(58) Field of Classification Search
CPC ............ A61B 17/072; A61B 17/07292; A61B 17/115
USPC ................ 227/19, 176.1; 604/288.04, 93.01; 424/400, 549, 642, 647, 682, 685, 698, 424/78.31; 514/15.2, 165, 17.2, 171, 54, 514/55, 567, 569, 57, 60, 9.2
See application file for complete search history.

(56) References Cited

U.S. PATENT DOCUMENTS

| | | | |
|---|---|---|---|
| 7,143,925 B2 | 12/2006 | Shelton, IV et al. | |
| 7,601,118 B2 | 10/2009 | Smith et al. | |
| 8,317,070 B2 | 11/2012 | Hueil et al. | |
| 8,393,514 B2 | 3/2013 | Shelton, IV et al. | |
| 9,282,962 B2 | 3/2016 | Schmid et al. | |
| 2008/0078804 A1* | 4/2008 | Shelton ................ | A61B 17/068 227/176.1 |
| 2009/0206125 A1* | 8/2009 | Huitema .......... | A61B 17/07207 227/175.1 |
| 2013/0221065 A1 | 8/2013 | Aronhalt et al. | |
| 2013/0256377 A1 | 10/2013 | Schmid et al. | |
| 2014/0027490 A1 | 1/2014 | Marczyk et al. | |
| 2015/0129634 A1 | 5/2015 | Shelton, IV et al. | |

(Continued)

FOREIGN PATENT DOCUMENTS

WO    WO-2013052435 A1    4/2013

OTHER PUBLICATIONS

Extended European Search Report for EP App. No. 18157118.3 dated May 8, 2018 (8 pages).

*Primary Examiner* — Nathaniel C Chukwurah
(74) *Attorney, Agent, or Firm* — Mintz Levin Cohn Ferris Glovsky and Popeo, P.C.

(57) ABSTRACT

Various adjunct releasing mechanisms are provided herein that can be incorporated into surgical devices, such as an end effector of a surgical stapler. For example, an adjunct releasing mechanism can act to release an adjunct attached to an end effector of a surgical stapler upon deployment of staples retained within the end effector. The adjunct can be retained on the end effector through a variety of means, such as through use of adhesive or by having a portion of the adjunct partially received within cavities formed on a tissue-facing surface of the end effector. The releasing mechanisms can extend into the cavities formed on the tissue-facing surface of the end effector to cause the adjunct to detach from the end effector upon deployment of staples.

14 Claims, 5 Drawing Sheets

(56) References Cited

U.S. PATENT DOCUMENTS

| | | |
|---|---|---|
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0272575 A1 | 10/2015 | Leimbach et al. |
| 2015/0277471 A1 | 10/2015 | Leimbach et al. |
| 2015/0351758 A1 | 12/2015 | Shelton, IV et al. |
| 2015/0351763 A1 | 12/2015 | Shelton, IV et al. |
| 2016/0089142 A1 | 3/2016 | Harris et al. |
| 2017/0055986 A1 | 3/2017 | Harris et al. |

* cited by examiner

ADJUNCT RELEASE FOR SURGICAL STAPLERS

FIELD

Methods, devices, and systems are provided for anchoring and releasing adjuncts from an end effector of a surgical device.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, various issues still exist. For example, leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. While these issues can be solved by application of various adjuncts to the tissue, it can be challenging to deliver these solutions to a tissue site and ensure proper placement. It can be desirable to have material securely attached to a surgical stapler during positioning and have material cleanly separate from the surgical stapler during use. Having materials both securely attached to and easily separable from surgical staplers can present problems. Thus there remains a need for improved devices, systems, and methods for attaching adjuncts to and releasing adjuncts from various surgical devices, such as surgical staplers.

SUMMARY

Various methods, devices, and systems are provided for anchoring and releasing adjuncts from an end effector of a surgical device.

In one embodiment, a staple cartridge assembly is provided for use with a surgical stapler that includes a cartridge body with a plurality of staple cavities on a tissue-facing surface thereof. Each staple cavity has a staple disposed therein that is configured to be deployed into tissue, and the cartridge body has a plurality of connection cavities on the tissue-facing surface. An adjunct is disposed on the tissue-facing surface of the cartridge body. A plurality of drivers is disposed within the cartridge body. Each driver has at least one adjunct releasing mechanism located thereon such that the plurality of drivers configured to cause the adjunct to detach from the cartridge body when the plurality of drivers are advanced into the staple cavities staples to deploy the staples.

The assembly can vary in numerous ways. For example, each connection cavity can be configured to receive a portion of the adjunct therein. The adjunct can have protrusions configured to be received in one or more of the plurality of connection cavities and configured to attach the adjunct to the cartridge body. In another example, the at least one adjunct releasing mechanism can include a post configured to extend into one of the plurality of connection cavities. In another example, the post can be configured to extend beyond the tissue-facing surface of the cartridge body to cause the adjunct to detach from the cartridge body. The adjunct can be releasably attached to the tissue-facing surface of the cartridge body with an adhesive. In some embodiments, the adhesive can be cyanoacrylate.

In another aspect, an end effector is provided for use with a surgical stapling instrument that includes a first jaw with a staple cartridge and a plurality of staple cavities configured to seat staples therein. An adjunct is attached to a tissue-facing surface of the cartridge and overlies the plurality of staple cavities. A second jaw has an anvil with a plurality of staple-forming cavities formed on a tissue-facing surface thereof, and the first and second jaws are configured to clamp the tissue therebetween. A plurality of drivers are disposed within the cartridge and configured to deploy a plurality of staples through the staple cavities, through the adjunct, and into tissue engaged between the first and second jaws, and to simultaneously cause the adjunct to detach from the cartridge.

The end effector can have a number of variations. For example, the adjunct can be attached to the tissue-facing surface of the cartridge by an adhesive. The cartridge can have at least one connection cavity formed in the tissue-facing surface thereof, and the adjunct can have at least one protrusion formed thereon that extends into the at least one connection cavity for attaching the adjunct to the cartridge. In some examples, each of the at least one connection cavities can be configured to receive a portion of one of the plurality of drivers therein. Each of the plurality of drivers can have a post that is configured to extend beyond the tissue-facing surface of the cartridge to cause the adjunct to detach from the cartridge.

In another aspect, a surgical method can be provided that includes advancing a surgical stapler into a body of a patient. The surgical stapler has an end effector at a distal end thereof with first and second jaws, and an adjunct attached to the first jaw of the end effector. The method includes engaging tissue between the first and second jaws of the end effector. The method also includes actuating the surgical stapler to cause a plurality of drivers to fire staples from the first jaw, through the adjunct, and into the tissue, and to cause the plurality of drivers to detach the adjunct from the first jaw.

The method can have numerous variations. For example, actuating the surgical stapler can cause a releasing member on each of the plurality of drivers to enter a connection cavity in a tissue-facing surface of the first jaw. In another example, actuating the surgical stapler can cause the releasing member to push a portion of the adjunct retained in the connection cavity out of the connection cavity to detach the adjunct from the first jaw. Actuating the surgical stapler can also cause the releasing member to engage the adjunct, thereby breaking an adhesive bond between the adjunct and the first to detach the adjunct from the first jaw.

BRIEF DESCRIPTION OF DRAWINGS

This invention will be more fully understood from the following detailed description taken in conjunction with the accompanying drawings, in which.

DETAILED DESCRIPTION

Figure 1:
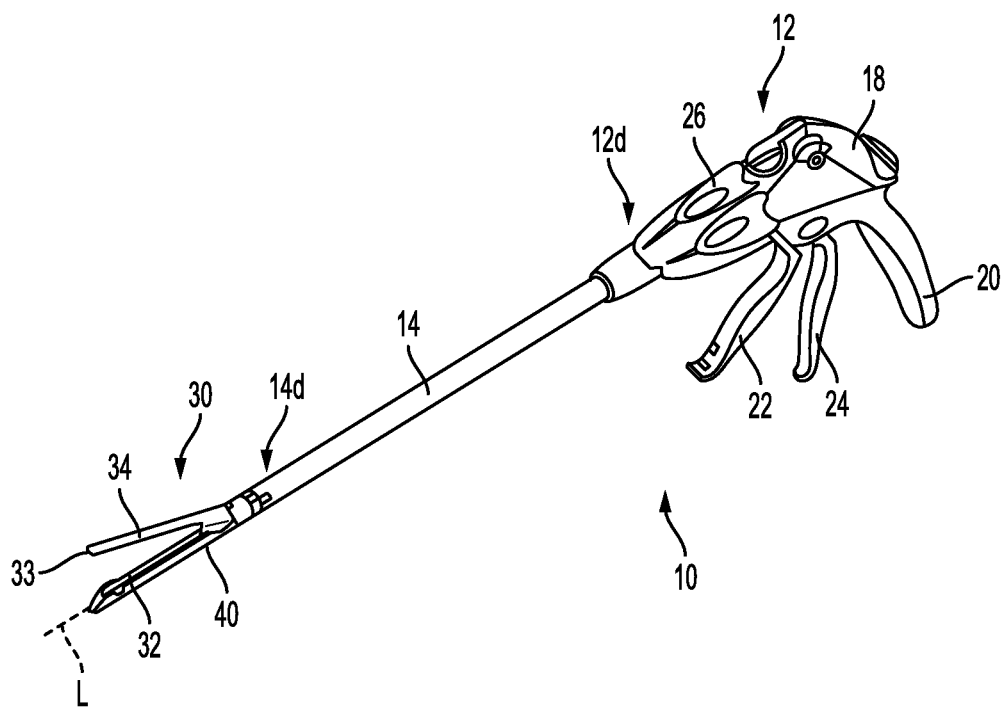
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

Various exemplary devices, systems, and methods for releasably retaining an adjunct material on an end effector of a surgical instrument are described herein. In some implementations, an adjunct material can be releasably retained on a jaw of an end effector in a manner that reduces or prevents the adjunct material from prematurely slipping off the jaw. In this way, the adjunct can be securely coupled to the end effector while a surgeon manipulates the end effector during a surgical procedure. The adjunct material can be coupled to an end effector in a variety of ways, for example by inserting portions of the adjunct into connection cavities on a tissue-facing surface of the jaw. In some embodiments, the adjunct can have tags or protrusions that extend from an outward facing surface such that the tags can be configured to be received in cavities on the tissue-facing surface of the jaw. In other implementations, the adjunct can be coupled to the tissue-facing surface of the jaw using an adhesive. The adjunct can remain coupled to the end effector until it is separated from the end effector and transferred to a treatment site in a patient, for example by a release mechanism that includes features and/or components that are configured for releasably attaching an adjunct thereto. A variety of release mechanisms can be used, such as staple deployment members and/or a cutting element that causes the adjunct to separate from the end effector. The release mechanism can thus allow a user to securely attach an adjunct to an end effector and allow the user to rapidly deploy the adjunct when desired.

The adjunct attachment and release techniques disclosed herein can be used in combination with a variety of surgical instruments, such as a surgical stapler. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The stapler can include a firing bar configured to drive the staples into tissue engaged between the jaws. The firing bar can include a knife or other cutting element capable of creating a cut between the staple rows along the tissue held within the jaws. The staplers can be used on a variety of tissues, for example in thoracic surgery or in gastric surgery.

Figure 2:
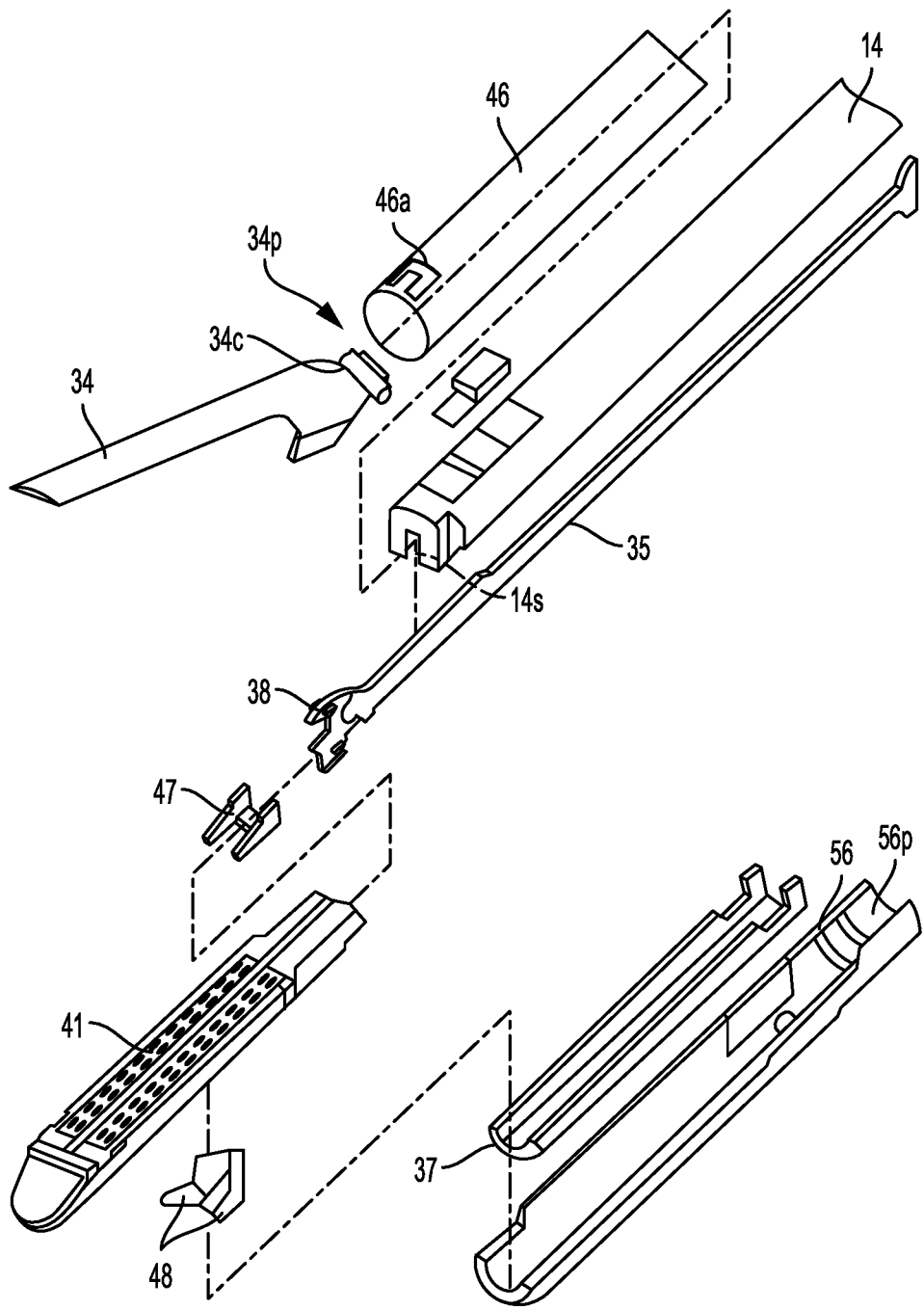
FIG. 2 is an exploded view of a distal portion of the surgical stapler of FIG. 1.

FIG. 1 illustrates one example of a linear surgical stapler 10. The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12*d* thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34*p* that is pivotally received within a proximal end 56*p* of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34*p* of the upper jaw 34 includes a closure feature 34*c* distal to its pivotal attachment with the staple channel 56. Thus, a closure tube 46, whose distal end includes a horseshoe aperture 46*a* that engages the closure feature 34*c*, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
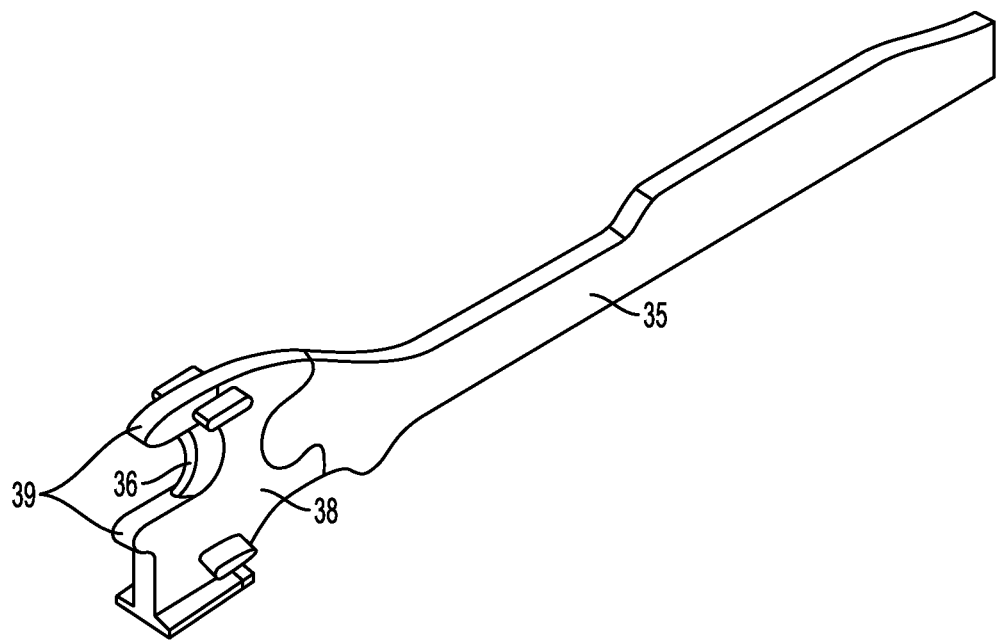
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14*s* of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
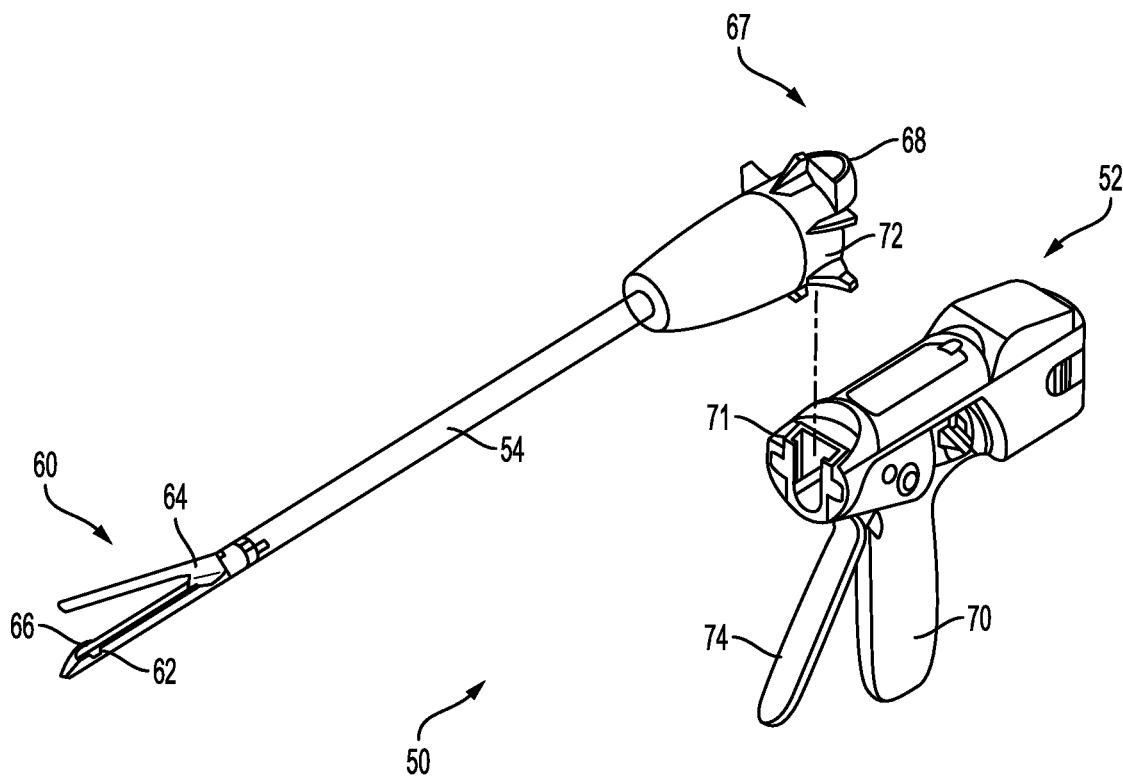
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

The illustrated examples of surgical stapling instruments 10, 50 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

A variety of different adjuncts can be used with the surgical instruments disclosed herein. "Adjuncts" are also referred to herein as "adjunct materials" or "buttresses." It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s).

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct. Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety. The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., in a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S. L.), hemostatic agents, and tissue healing agents.

The adjuncts can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Figure 5:
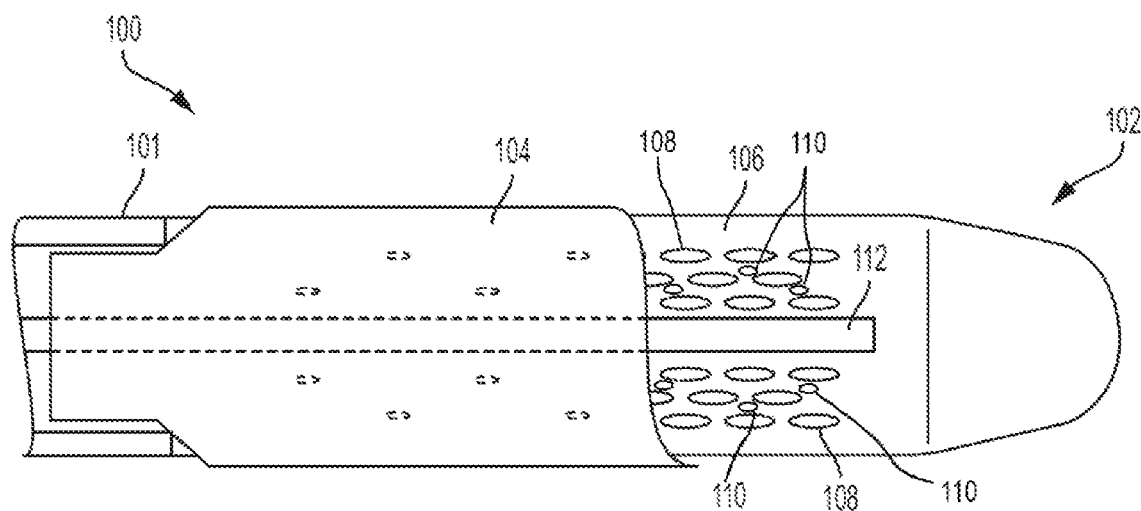
FIG. 5 is a top view of a lower jaw member of a surgical stapler showing a portion of an adjunct disposed thereon.
Figure 6:
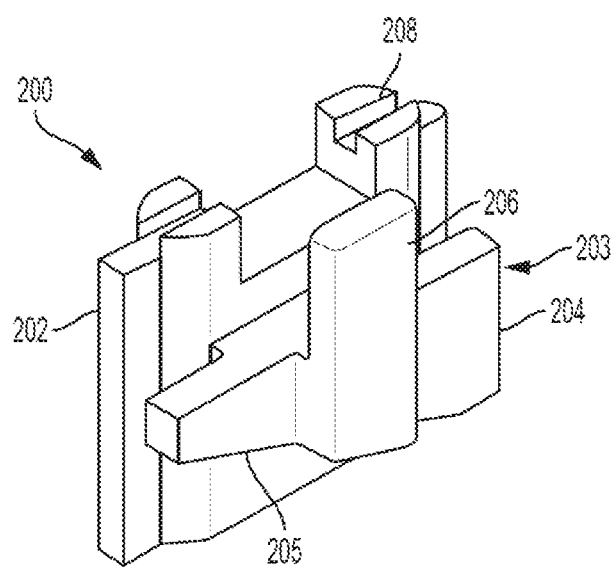
FIG. 6 is a perspective view of a single staple driver with an adjunct releasing mechanism.
Figure 7:
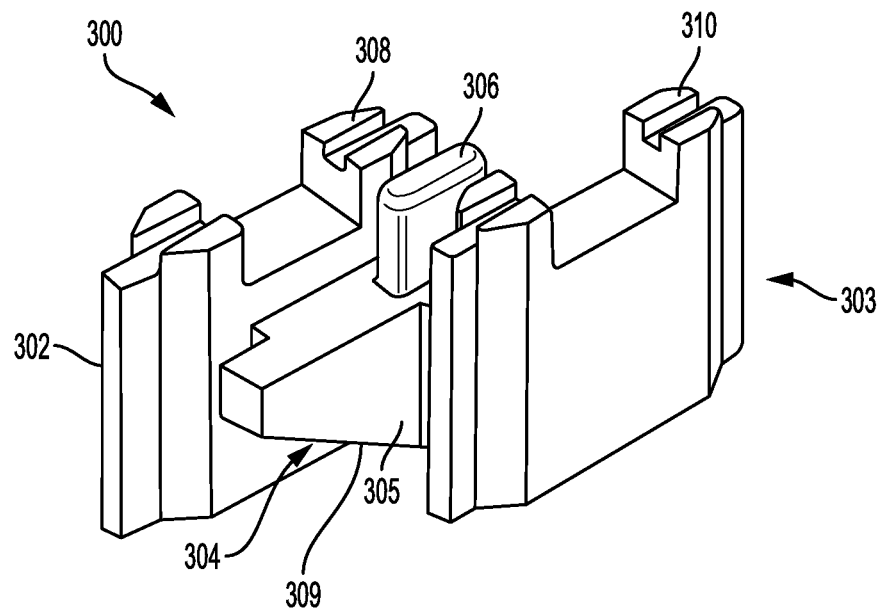
FIG. 7 is a perspective view of a double staple driver with an adjunct releasing mechanism.

Use of buttresses, adjuncts, and/or medicants with various surgical devices, such as surgical staplers, can necessitate attaching and releasing the adjunct from at least one tissue-contacting surface of an end effector, as discussed above. Attaching an adjunct to and releasing an adjunct from an end effector can be achieved through a variety of techniques. FIGS. 5-7 illustrate one embodiment of an end effector 100 having an adjunct releasing mechanism. FIG. 5 illustrates a portion of a lower jaw 101 of the end effector 100, which can be disposed on a distal end of a surgical instrument, such as surgical staplers 10, 50 discussed above. The lower jaw 101 can have a cartridge 102 disposed thereon, similar to the staple cartridge 40, that has a tissue-facing surface 106 with an adjunct 104 (only a portion of the adjunct 104 is shown) disposed thereon, such as one or more of the buttresses, adjuncts, and/or medicants discussed above.

The cartridge 102 can have staples disposed in staple cavities 108 which are formed in the tissue-facing surface 106. The tissue-facing surface 106 can also have a channel 112 configured to receive a cutting element, similar to the knife blade 36, as it moves distally therethrough. One or more connection cavities 110 can extend between and connect the staple cavities 108 for attaching an adjunct to the cartridge 102. The connection cavities 110 can be in the form of recesses or bores, and can have a variety of configurations and shapes. For example, the connection cavities 110 can be roughly oval in shape and smaller than the staple cavities 108. In other embodiments, the cavities can be circular, square, rectangular, 3-dimensional shapes, etc., and they can be larger than, equal in size to, or a combination of sizes relative to the staple cavities 108. The cavities 110 can be disposed between rows of the staple cavities 108. However, the connection cavities 110 can have any number of configurations, such as each staple cavity 108 having a connection cavity 110 adjacent thereto. While the connection cavities 110 are formed adjacent to the staple cavities 108 on the tissue-facing surface 106, they can be formed elsewhere. For example, the cavities can be formed at the interface of the cartridge and a tray, similar to tray 37, such that some portion of the inner surface of the cavity is a surface of the cartridge, and another portion is a surface of the tray. Furthermore, connection cavities for attaching and detaching an adjunct need not be limited to the tissue-facing surface of the cartridge. For example, connection cavities can be formed along the edge of the tissue-facing surface of the cartridge such that when the end effector is assembled, a portion of the connection cavity will be formed by a staple tray similar to staple tray 37. Alternatively, rather than connection cavities, a channel can be formed between the tissue-facing surfaces of the cartridge and the tray. Portions of the adjunct can be tucked into the channel, or adhered to the tissue-facing surface at locations proximal to the channel, during manufacturing or at any time prior to use. In such an embodiment, drivers near the outermost edge of the tissue-facing surface of the cartridge can have an adjunct releasing mechanism such that portions of the adjunct are pushed out of the channel, and/or break the adhesive bond along the channel between the adjunct and the cartridge during firing.

The adjunct 104 can be configured to be releasably retained on the tissue-facing surface 106. The adjunct 104 can have protrusions or tabs disposed on a surface that contacts the tissue-facing surface 106, and the protrusions can be configured to extend into and engage with the connection cavities 110. The adjunct 104 can be configured to engage the tissue-facing surface 106 through a variety of means. For instance, protrusions on the adjunct can be received in the connection cavities and securely attaching due to a friction fit attachment. In such an example, an adjunct can be created by extruding a film such that it has protrusions in predefined locations that correspond to locations of the connection cavities on a tissue-facing surface of a cartridge. In other embodiments, the adjunct can be made from a VICRYL® (polyglactin 910) material, and can include one or more backing layers made of polydioxanone (PDS). The one or more PDS layers can be fused to the VICRYL® material, and the one or more PDS layers can include protrusions that can be configured to extend into and mate with the connection cavities. In addition or alternatively, the adjunct can engage the tissue-facing surface through use of an adhesive, such as cyanoacrylate.

The cartridge 102 can have one or more staple drivers 200, 300 movably disposed therein, similar to staple drivers 48. The staple drivers 200, 300 can be configured to move upward through the staple cavities 108 to apply an upward force on each of the plurality of staples within the cartridge 102. The staple driver 200 illustrated in FIG. 6 can have a staple portion 202 that can have a staple channel 208 formed on an upper end thereon and that can be configured to seat a staple therein, similar to the staple driver 48. The driver 200 can also have an adjunct releasing mechanism 203 attached to a side of the staple portion 202 and having a generally L-shaped configuration. The adjunct releasing mechanism 203 can have a connecting element 204 that connects the staple portion 202 to the adjunct releasing mechanism 203. A post 206 can be attached to the connecting element 204 and it can extend upward in the same direction as the staple channel 208 of the staple portion 202. The connecting element 204 can have an upward-angled bottom 205 that is configured to contact a wedge sled, similar to the wedge sled 47, to allow upward movement of the driver 200 and firing of the staples. The post 206 can have a variety of shapes, such as a rectangular shape as illustrated in FIG. 6, a cylindrical shape, a square, etc. In an exemplary embodiment, the post 206 has a shape that corresponds to a shape of the connection cavity 110 such that the post 206 can be received in the connection cavity 110.

FIG. 7 illustrates another embodiment of a staple driver 300 that can be configured similar to the staple driver 200. However, staple driver 300 can have first and second staple portions 302, 303 similar to the staple portion 202 with staple channels 308, 310 disposed on upper ends of the staple portions 302, 303, respectively. Each staple channel 308, 310 can be configured to seat a staple therein, and the staple driver 300 can be configured to fire two staples simultaneously. The first and second staple portions 302, 303 can have an adjunct releasing mechanism 304 coupled therebetween. The adjunct releasing mechanism 304 can include a connecting element 305 and a post 306. The connecting element 305 extends between and connects the two staple portions 302, 303, and it has an upward-angled bottom 309 that is configured to contact a wedge sled, similar to the wedge sled 47, to allow upward movement of the driver 300 and firing of the staples. The post 306 is attached to the connecting element 305 and extends upward in the same direction as the staple channels 308, 310. The post 306 can have a variety of shapes, such as a rectangular shape as illustrated in FIG. 6, a cylindrical shape, a square, etc. In an exemplary embodiment, the post 306 has a shape that corresponds to a shape of the connection cavity 110 such that the post 306 can be received in the connection cavity 110.

While the illustrated staple drivers 200, 300 have connecting elements between the staple portions and the adjunct releasing mechanisms, a variety of connections can be used to connect multiple staple drivers. For example, two connecting elements can be used to connect three staple drivers. One skilled in the art will appreciate that a connecting element can include multiple adjunct releasing mechanisms, that multiple connecting elements can be used in parallel or in series to connect multiple staple drivers, and that the adjunct releasing mechanisms can have any number of geometries. For example, the adjunct releasing mechanisms can be curved, or can have cross-sections that are square, circular, triangular, etc. Additionally, it is possible that not all of the adjunct releasing mechanisms are uniform. The adjunct releasing mechanisms can have sharp features, as well. For example, the detachment features can be sharpened such that they can cut away a small portion of the adjunct to detach the rest from a tissue-facing surface of a cartridge.

In use, the staple drivers 200 and/or 300 can be disposed in the cartridge 102 and aligned with the staple cavities 108 and the connection cavities 110 such that the staple channels 208, 308, 310 are aligned with the staple cavities 108 and the posts 206, 306 are aligned with the connection cavities 110. The cartridge 102 can be loaded with staples. The adjunct 104 can be retained on the tissue-facing surface 106 by, for example, having a plurality of protrusions friction fit within the connection cavities 110. The adjunct 104 can be applied to the tissue-facing surface 106 any time before use, such as during manufacture or during preparation for use, and can be applied through a variety of techniques, such as by use of an applicator.

A surgeon can maneuver the surgical stapler into position and clamp tissue between jaws of the end effector 100 thereon. The surgeon can then fire the surgical stapler, causing a sled, similar to wedge sled 47, to move distally through the cartridge 102 of the end effector 100. The sled can push one or more of the staple drivers 200, 300 upwardly through the staple cavities 108 in the staple cartridge 102. Upward movement of the staple drivers 200, 300 applies an upward force on each of the plurality of staples within the cartridge 102 to thereby push the staples upwardly through the adjunct 104 and tissue and against an anvil surface of an upper jaw of the end effector 100 to form the staples. Upward movement of the staple drivers 200, 300 also moves the posts 206, 306 upwards. The posts 206, 306 apply an upward force on the protrusions of the adjunct 104, forcing the protrusions out of the connection cavities 110 as distal ends of the posts 206, 306 enter the cavities 110. Forcing the protrusions from the cavities 110 releases the adjunct 104 from the tissue-facing surface 106, and the adjunct can be secured by staples to the tissue grasped by the end effector 100. In other embodiments, the posts 206, 306 can be configured to force the protrusions only partially out of the connection cavities 110, which can be sufficient to loosen the adjunct 104 from the tissue-facing surface 106 enough such that the staples will remove the adjunct 104 entirely upon firing. In various embodiments, firing the surgical stapler can also cause a cutting element to translate through the cartridge 102 along the channel 112 to tissue while staples are fired and the adjunct 104 is released.

Figure 8:
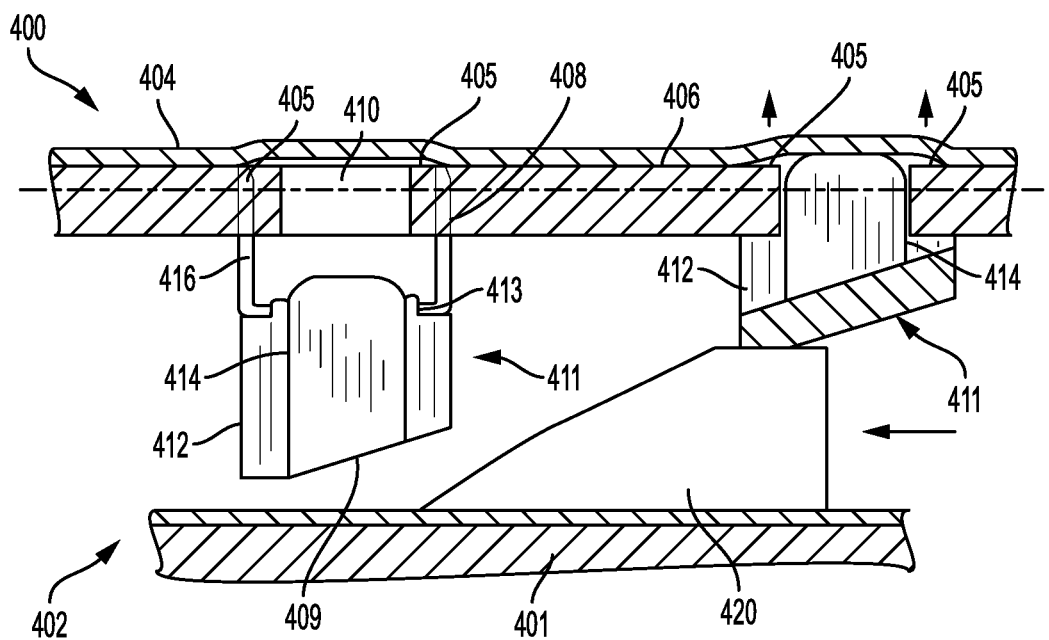
FIG. 8 is a cross-sectional side view of another embodiment of a portion of a lower jaw member of a surgical stapler with an adjunct releasing mechanism.

While the adjunct 104 can be attached to the cartridge 102 by protrusions, as noted above, adjuncts can be attached to a cartridge of a surgical stapler through a variety of means. For example, FIG. 8 illustrates an end effector 400 with a cartridge 402 and an adjunct 404 secured thereto by an adhesive. The end effector 400 can generally function and include components similar to end effector 100. For example, the end effector 400 can include an upper jaw having an anvil (not shown) and a lower jaw 401 with the cartridge 402 engaged thereon.

The cartridge 402 can have staples 416 disposed in a plurality of staple cavities 408 and a plurality of connection cavities 410 formed in a tissue-facing surface 406. The connection cavities 410 can have a variety of configurations and shapes. For example, the connection cavities 410 can be roughly oval in shape and smaller than the staple cavities 408. In other embodiments, the connection cavities 410 can be circular, square, rectangular, etc., and they can be larger than, equal in size to, or a combination of sizes relative to the staple cavities 408. The connection cavities 410 can be disposed between rows of the staple cavities 408. However, the connection cavities 410 can have any number of configurations.

The adjunct 404 can be configured to be releasably retained on the tissue-facing surface 406, and the adjunct 404 can be any of the adjuncts discussed herein. The adjunct 404 can have adhesive disposed on a surface that contacts the tissue-facing surface 406. For example, there can be adhesive points 405 between the adjunct 404 and the tissue-facing surface 406 around outer edges of the connection cavities 410 that can be configured to retain the adjunct 404 on the cartridge 402. However, a variety of different placements of the adhesive points 405 is possible, such as in a grid pattern. Additionally, the adhesive can be spread uniformly on the tissue-facing surface 406. A variety of adhesives can be used, such as cyanoacrylate.

When the adjunct is attached to the cartridge with an adhesive, it can be desirable in various embodiments to prevent the adhesive from spilling into the cartridge, for example into a cutting element channel or into the staple cavities. Various adjuncts can be configured to include features that prevent or inhibit adhesive from spilling into the cartridge and/or specifically the cutting element channel of the cartridge during the attachment process. As an example, the adhesive points 405 can be formed by including small circular molded features on a surface of the adjunct 404 that contacts the tissue-facing surface 406 of the cartridge 404. The circular molded features can act as reservoirs to form adhesive droplet attachment point insuring the adhesive, such as cyanoacrylate, does not enter the cartridge 402 and/or the cutting element channel during attachment. In other embodiments, the adhesive can be housed within the adjunct itself, or reservoirs for adhesive can be part of an applicator used to apply the adjunct to the cartridge. For example, the reservoirs can be broken as part of clamping or pulling an activation lever on the applicator.

The cartridge 402 can have one or more staple drivers 411 movably disposed therein, similar to staple drivers 200, 300, that can be configured to move upward through staple cavities 408 to apply an upward force on each of the plurality of staples 416 within the cartridge 402. Each staple driver 411 can have a staple portion 412 that can have a staple channel 413 formed on an upper end thereof that is configured to seat a staple 416 therein. The driver 411 can also have an adjunct releasing mechanism attached to a side of the staple portion 412 and having a post 414 that is attached to the staple portion 412 and that extends upward in the same direction as the staple channel 413 of the staple portion 412. The staple driver 411 can have an upward-angled bottom 409 that is configured to receive a wedge sled 420, similar to the wedge sled 47, to allow upward movement of the driver 200 and firing of the staple. The post 414 can have a variety of shapes, such as a rectangular shape, a cylindrical shape, a square shape, etc., and the post 406 can be configured to be received in the connection cavities 410.

In use, the cartridge 402 can have a plurality of the staple drivers 411 disposed therein and loaded with staples 416. The adjunct 404 can be retained on the tissue-facing surface 406 by, for example, having a plurality of adhesive points 405 between the adjunct 404 and the tissue-facing surface 406 around the outer edges of the connection cavities 410. The adjunct 404 can be applied to the tissue-facing surface 406 any time before use, such as during manufacture or during preparation for use, and can be applied through a variety of techniques, such as by use of an applicator. A surgeon can maneuver the surgical stapler into position and clamp tissue between jaws of the end effector 400 thereon. The surgeon can then fire the surgical stapler, causing the sled 420 to move distally through the cartridge 402 of the end effector 400. The sled 420 can push one or more of the staple drivers 411 upwardly through the staple cavities 408 in the staple cartridge 402. Upward movement of the staple drivers 411 applies an upward force on each of the plurality of staples 416 within the cartridge 402 to thereby push the staples upwardly through the adjunct 404 and tissue and against an anvil surface of the upper jaw of the end effector 400 to form the staples. Upward movement of the staple drivers 411 also moves the posts 414 upwards. The posts 414 can apply an upward force on the adjunct 404, forcing the adjunct 404 to move upwards and breaking the adhesive points 405 once the posts 414 move sufficiently through the connection cavities 411. For example, the adhesive points 405 can hold firm until a distalmost end of the posts 414 crosses a plane of the tissue-facing surface 406. Breaking, cracking, or separating the adhesive points 405 from between the adjunct 404 and the tissue-facing surface 406 releases the adjunct 404 from the tissue-facing surface 406, and the adjunct 404 can be secured by the staples 416 to the tissue grasped by the end effector 400. Although a distalmost end of the posts 414 can cross a plane of the tissue-facing surface 406, the posts 414 can be configured such that they only extend even with, or below, the tissue-facing surface 406. In some embodiments, firing the surgical stapler can also cause a cutting element to translate through the cartridge 402, cutting tissue while the staples 416 are fired and the adjunct 404 is released.

While an adjunct can be attached to a lower jaw as illustrated above, an adjunct can also be attached to components of the upper jaw, such as the anvil. The upper jaw can be similar to that shown in FIGS. 1-2, but can include features and/or components for attaching and detaching an adjunct. For example, the upper jaw can be configured to include connection cavities and drivers that are driven by an E-beam to cause the adjunct to detach from the jaw. In various embodiments, when stapling is initiated, the components of the lower jaw can function to drive staples through tissue and the adjunct, while the drivers in the upper jaw can function to detach the adjunct from the anvil.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A staple cartridge assembly for use with a surgical stapler, comprising:
    a cartridge body having a plurality of staple cavities on a tissue-facing surface thereof, each staple cavity having a staple disposed therein that is configured to be deployed into tissue, and the cartridge body having a plurality of connection cavities separate from the plurality of staple cavities on the tissue-facing surface;
    an adjunct disposed on the tissue-facing surface of the cartridge body, the adjunct having a plurality of protrusions disposed on an adjunct surface configured to contact the tissue-facing surface, the plurality of protrusions being configured to extend into and engage with the plurality of connection cavities; and
    a plurality of drivers disposed within the cartridge body, each driver having at least one adjunct releasing mechanism located thereon such that the plurality of drivers are configured to drive the plurality of protrusions of the adjunct out of the plurality of connection cavities and cause the adjunct to detach from the cartridge body when the plurality of drivers are advanced into the staple cavities to deploy the staples.

2. The staple cartridge assembly of claim 1, wherein the at least one adjunct releasing mechanism comprises a post configured to extend into one of the plurality of connection cavities.

3. The staple cartridge assembly of claim 2, wherein the post is configured to extend beyond the tissue-facing surface of the cartridge body to cause the adjunct to detach from the cartridge body.

4. The staple cartridge assembly of claim 1, wherein the adjunct is releasably attached to the tissue-facing surface of the cartridge body with an adhesive.

5. The staple cartridge assembly of claim 4, wherein the adhesive is cyanoacrylate.

6. An end effector for use with a surgical stapling instrument, comprising:
    a first jaw having a staple cartridge with a plurality of staple cavities configured to seat staples therein, and an adjunct attached to a tissue-facing surface of the cartridge and overlying the plurality of staple cavities;
    a second jaw having an anvil with a plurality of staple-forming cavities formed on a tissue-facing surface thereof, the first and second jaws being configured to clamp the tissue therebetween; and
    a plurality of drivers disposed within the cartridge and configured to deploy a plurality of staples through the staple cavities, through the adjunct, and into tissue engaged between the first and second jaws, and to simultaneously cause the adjunct to detach from the cartridge, wherein the cartridge has a plurality of connection cavities formed in the tissue-facing surface thereof and separate from the plurality of staple cavities, and the adjunct has a plurality of protrusions formed thereon configured to extend into the plurality of connection cavities for attaching the adjunct to the cartridge.

7. The end effector of claim 6, wherein the adjunct is attached to the tissue-facing surface of the cartridge by an adhesive.

8. The end effector of claim 6, wherein each of the plurality of connection cavities is configured to receive a portion of one of the plurality of drivers therein.

9. The end effector of claim 6, wherein each of the plurality of drivers has a post that is configured to extend beyond the tissue-facing surface of the cartridge to cause the adjunct to detach from the cartridge.

10. A staple cartridge assembly for use with a surgical stapler, comprising:
   a cartridge body having a plurality of staple cavities and a plurality of connection cavities on a tissue-facing surface thereof, each staple cavity having a staple disposed therein that is configured to be deployed into tissue;
   an adjunct disposed on the tissue-facing surface of the cartridge body, the adjunct having a plurality of protrusions configured to engage with the plurality of connection cavities to secure the adjunct thereto; and
   a plurality of drivers disposed within the cartridge body, each driver having at least one staple portion configured to seat a staple therein and to deploy the staple therefrom, each driver having at least one adjunct releasing mechanism located thereon and being configured to drive the plurality of protrusions out of the plurality of connection cavities to release the adjunct from the cartridge body, the at least one adjunct releasing mechanism being configured to extend beyond the tissue-facing surface of the cartridge body when releasing the adjunct while the at least one staple portion being configured to deploy a corresponding staple without extending beyond the tissue-facing surface of the cartridge body.

11. The staple cartridge assembly of claim 10, wherein each staple portion has a staple channel formed on an upper end thereof configured to seat a staple and drive the staple through tissue during deployment; and
   wherein each adjunct releasing mechanism has a post extending in a same direction as the staple channel of the corresponding staple portion.

12. The staple cartridge assembly of claim 10, wherein the plurality of connection cavities are disposed adjacent to the plurality of staple cavities on the tissue-facing surface.

13. The staple cartridge assembly of claim 10, wherein each driver has a connecting element that connects the staple portion to the adjunct releasing mechanism.

14. The staple cartridge assembly of claim 10, wherein each driver comprises two staple portions connected to each other by a single adjunct releasing mechanism.

\* \* \* \* \*